United States Patent
Yoon

(10) Patent No.: US 10,042,203 B2
(45) Date of Patent: Aug. 7, 2018

(54) OPTICAL MEMBER, DISPLAY DEVICE HAVING THE SAME AND METHOD OF FABRICATING THE SAME

(75) Inventor: Yeo Eun Yoon, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 504 days.

(21) Appl. No.: 14/354,872

(22) PCT Filed: Aug. 16, 2012

(86) PCT No.: PCT/KR2012/006521
§ 371 (c)(1),
(2), (4) Date: Apr. 28, 2014

(87) PCT Pub. No.: WO2013/062222
PCT Pub. Date: May 2, 2013

(65) Prior Publication Data
US 2014/0285998 A1    Sep. 25, 2014

(30) Foreign Application Priority Data

Oct. 28, 2011  (KR) .................. 10-2011-0111679

(51) Int. Cl.
*G02F 1/1335*  (2006.01)
*G02F 1/13357*  (2006.01)
(Continued)

(52) U.S. Cl.
CPC .............. *G02F 1/1336* (2013.01); *C07F 9/12* (2013.01); *F21V 9/30* (2018.02); *G02B 6/005* (2013.01);
(Continued)

(58) Field of Classification Search
CPC ........... C07F 9/12; F21V 9/16; G02B 6/0023; G02B 6/0041; G02B 6/005; G02B 6/0065;
(Continued)

(56) References Cited

U.S. PATENT DOCUMENTS 6,501,091 B1 * 12/2002 Bawendi ................ B82Y 10/00
257/100
2002/0137821 A1   9/2002 Seidel et al.
(Continued)

FOREIGN PATENT DOCUMENTS

EP          2214219 A2    8/2010
JP       2002-365429 A   12/2002
(Continued)

OTHER PUBLICATIONS

European Search Report dated Sep. 23, 2015 in European Application No. 12843682.1.
(Continued)

*Primary Examiner* — Michael B Nelson
(74) *Attorney, Agent, or Firm* — Saliwanchik, Lloyd & Eisenschenk

(57) ABSTRACT

Disclosed are an optical member, a display device including the same, and a method of fabricating the same. The optical member includes a first substrate; a wavelength conversion layer on the first substrate; and a second substrate on the wavelength conversion layer, wherein the wavelength conversion layer includes an oxygen barrier.

4 Claims, 6 Drawing Sheets

(51) Int. Cl.
*C07F 9/12* (2006.01)
*F21V 8/00* (2006.01)
*F21V 9/30* (2018.01)

(52) U.S. Cl.
CPC ......... *G02B 6/0023* (2013.01); *G02B 6/0041* (2013.01); *G02F 1/133615* (2013.01); *G02B 6/0065* (2013.01); *G02F 2001/133614* (2013.01)

(58) Field of Classification Search
CPC .............. G02F 1/1336; G02F 1/133615; G02F 2001/133614
See application file for complete search history.

(56) References Cited

U.S. PATENT DOCUMENTS

| | | | |
|---|---|---|---|
| 2002/0186461 A1 | 12/2002 | Saiki | |
| 2004/0012844 A1 | 1/2004 | Ohtsuki et al. | |
| 2004/0251809 A1* | 12/2004 | Shimomura | C09K 11/0883 313/485 |
| 2006/0226774 A1* | 10/2006 | Sofue | C08G 77/18 313/512 |
| 2007/0146887 A1 | 6/2007 | Ikeda et al. | |
| 2008/0231170 A1* | 9/2008 | Masato | C09K 11/565 313/501 |
| 2009/0218041 A1* | 9/2009 | Dean | C09J 5/00 156/305 |
| 2010/0052504 A1 | 3/2010 | Sato et al. | |
| 2010/0187962 A1* | 7/2010 | Shin | H01L 33/56 313/1 |
| 2011/0034597 A1* | 2/2011 | Moy | C07F 9/12 524/127 |
| 2011/0263760 A1* | 10/2011 | Jakupca | C08G 79/04 524/91 |

FOREIGN PATENT DOCUMENTS

| | | |
|---|---|---|
| JP | 2005-126518 A | 5/2005 |
| JP | 2005-128140 A | 5/2005 |
| KR | 10-2006-0111622 A | 10/2006 |
| KR | 10-2011-0012246 A | 2/2011 |
| WO | WO-2008/027536 A1 | 3/2008 |

OTHER PUBLICATIONS

Office Action dated Dec. 15, 2014 in Taiwanese Application No. 101133158.
International Search Report in International Application No. PCT/KR2012/006521, filed Aug. 16, 2012.

* cited by examiner

[Fig. 1]
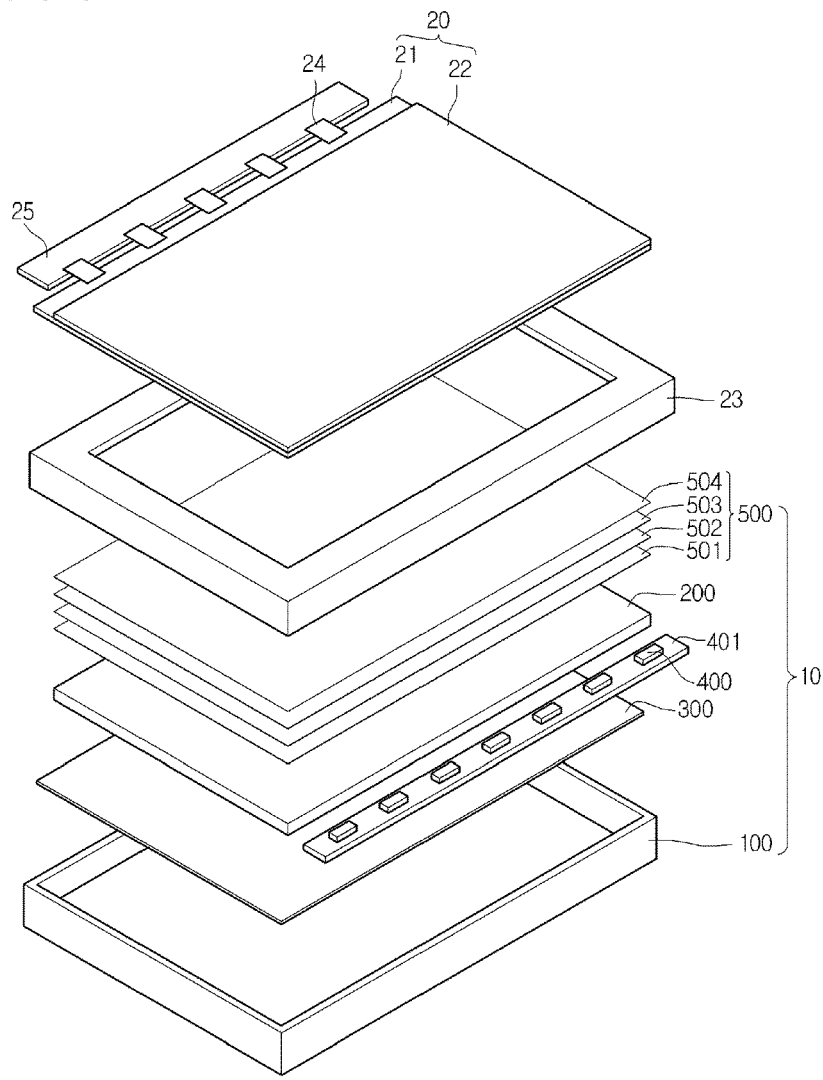
[Fig. 2]
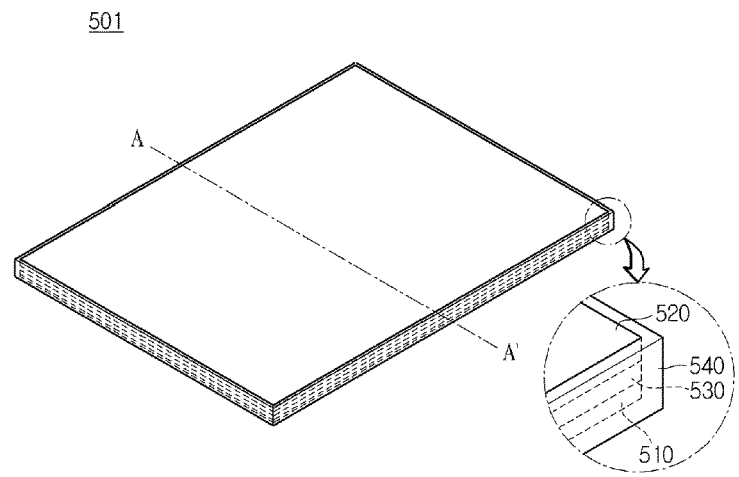

[Fig. 3]
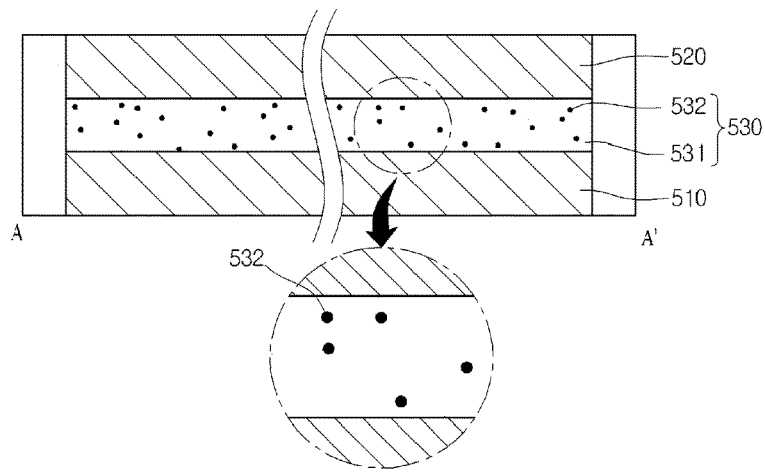
[Fig. 4]
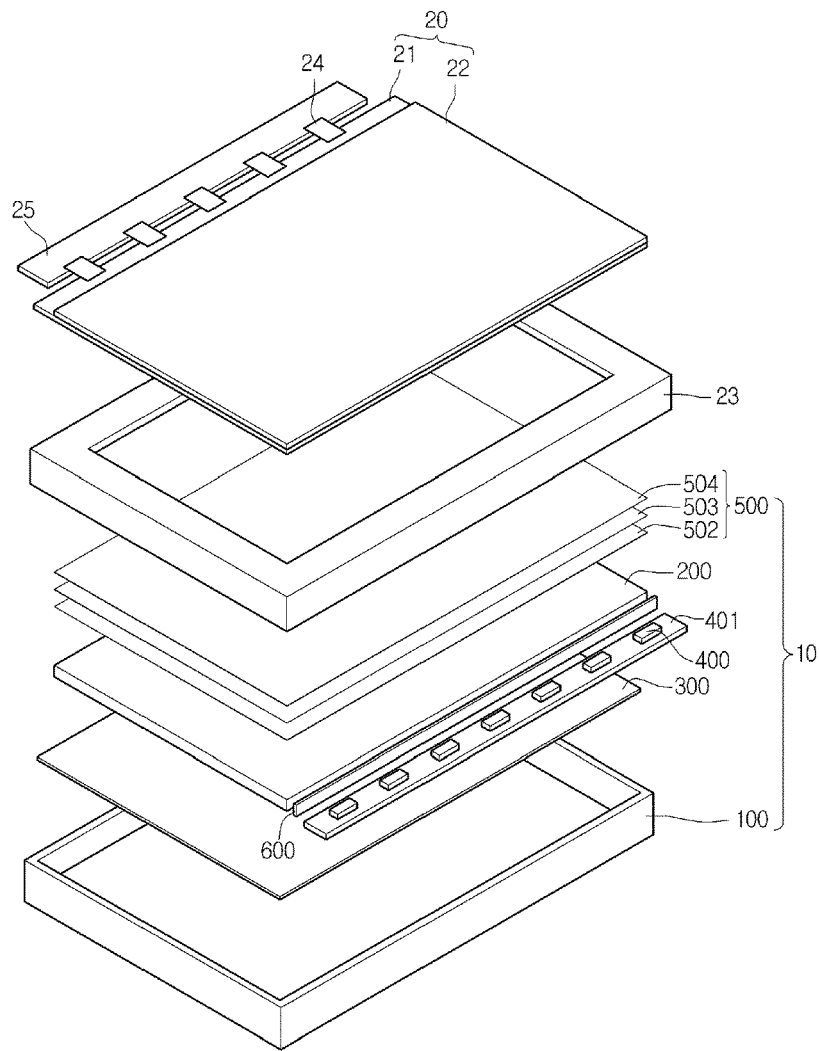

[Fig. 5]
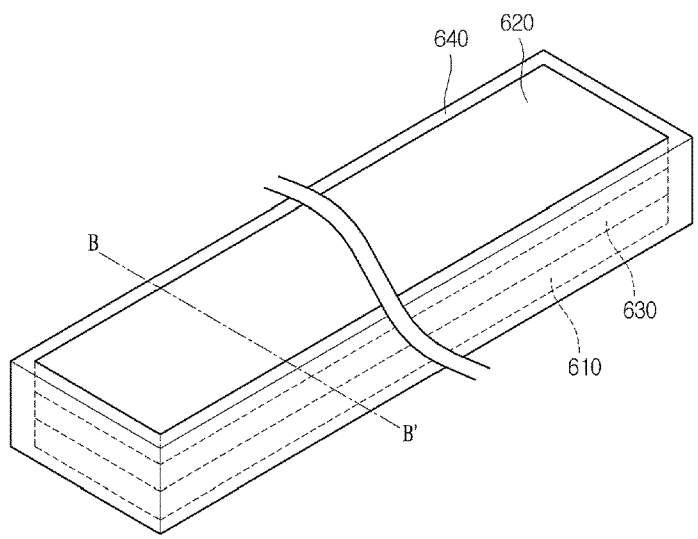
[Fig. 6]
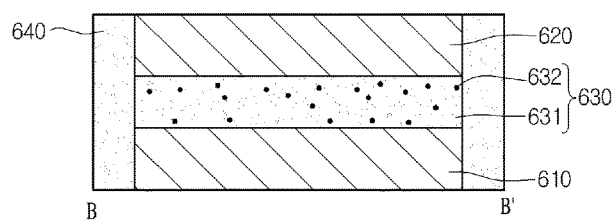
[Fig. 7]
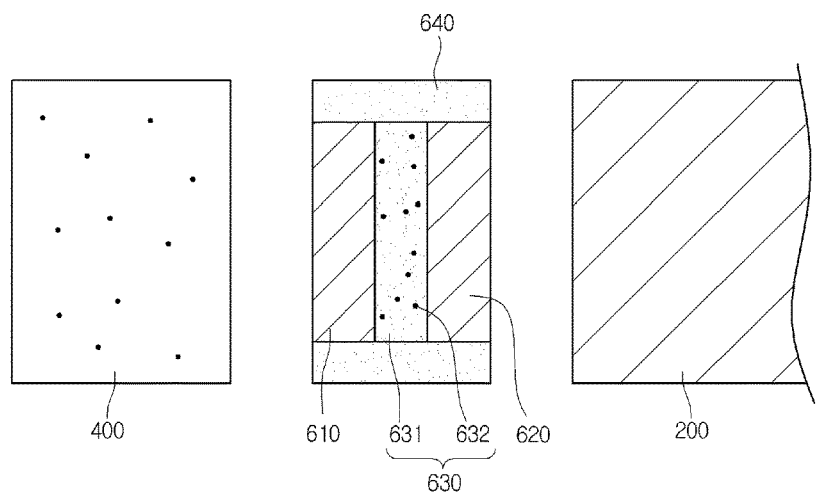
[Fig. 8]
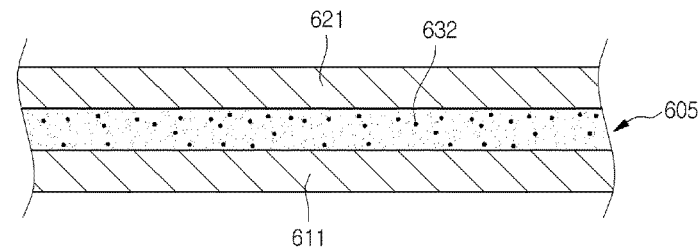

[Fig. 9]
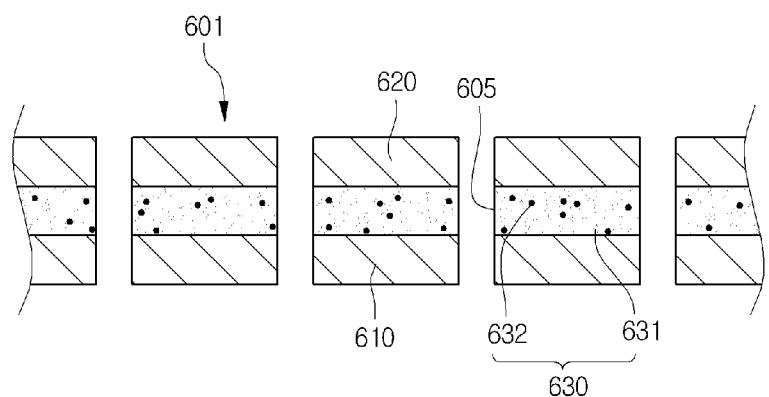
[Fig. 10]
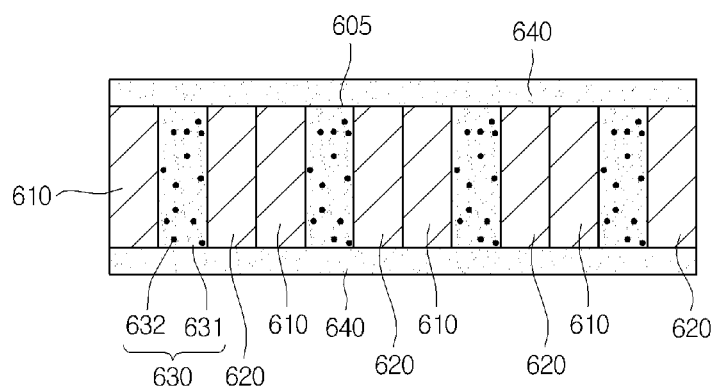

[Fig. 11]
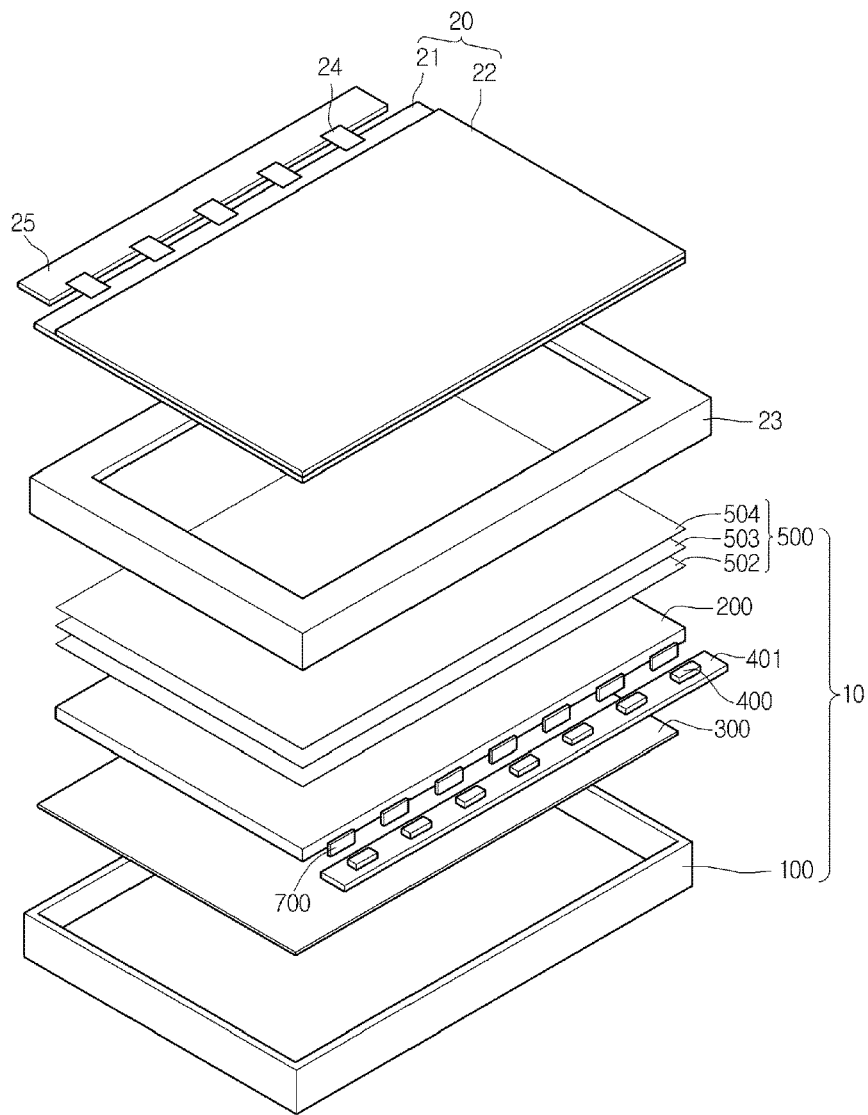
[Fig. 12]
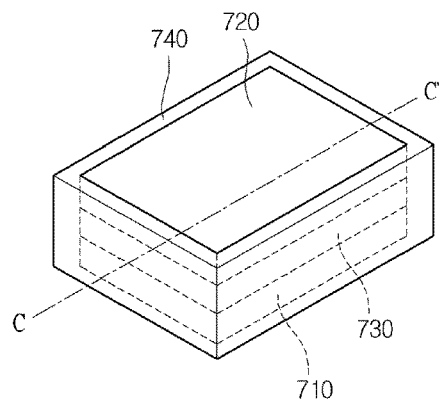

[Fig. 13]
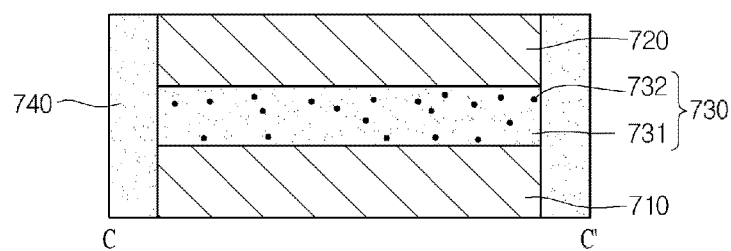
[Fig. 14]
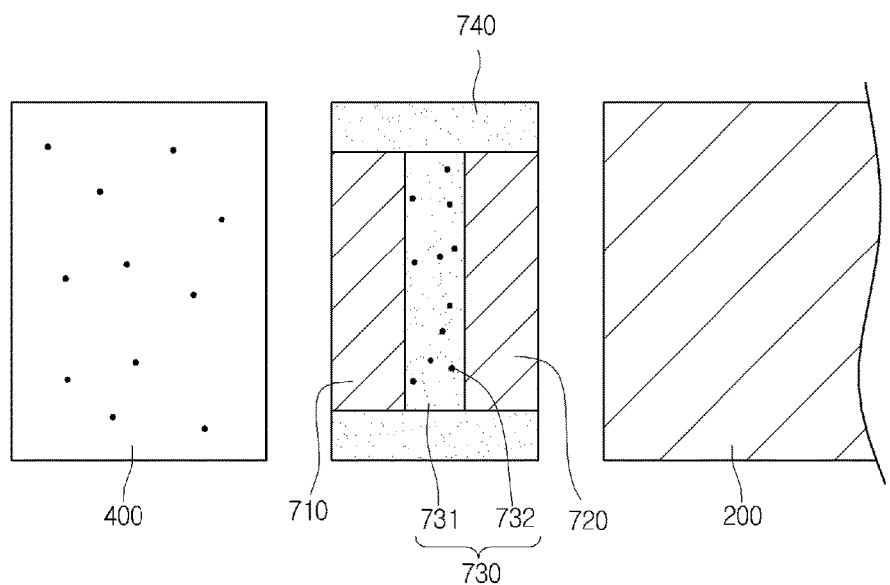

OPTICAL MEMBER, DISPLAY DEVICE HAVING THE SAME AND METHOD OF FABRICATING THE SAME

CROSS-REFERENCE TO RELATED APPLICATIONS

This application is the U.S. national stage application of International Patent Application No. PCT/KR2012/006521, filed Aug. 16, 2012, which claims priority to Korean Application No. 10-2011-0111679, filed Oct. 28, 2011, the disclosures of each of which are incorporated herein by reference in their entirety.

TECHNICAL FIELD

The embodiment relates to an optical member, a display device having the same, and a method of fabricating the same.

BACKGROUND ART

Some display devices require a backlight unit for generating light to display images. The backlight unit is a device for supplying the light to a display panel including liquid crystal and includes a light emitting device and means for effectively transferring the light emitted from the light emitting device to the liquid crystal.

A light emitting diode (LED) can be used as a light source for the display device. In addition, a light guide plate and optical sheets may be laminated in the display device to effectively transfer the light generated from the light source to the display panel.

An optical member that converts the wavelength of the light generated from the light source such that white light can be incident into the light guide plate or the display panel can be employed in the display device. In particular, quantum dots may be used to convert the wavelength of the light.

The quantum dot has a particle size of 10 nm or less and the electric and optical characteristics of the quantum dot may vary depending on the particle size thereof. For instance, if the quantum dot has the particle size in the range of about 55 Å to about 65 Å, light having a red color can be emitted. In addition, if the quantum dot has the particle size in the range of about 40 Å to about 50 Å, light having a green color can be emitted and if the quantum dot has the particle size in the range of about 20 Å to about 35 Å, light having a blue color can be emitted. The quantum dot emitting light having a yellow color may have the intermediate particle size between the particle sizes of the quantum dots emitting the red and green colors. The color of the spectrum according to the wavelength of the light tends to be shifted from the red color to the blue color, so it is estimated that the size of the quantum dot may be sequentially changed from 65 Å to 20 Å and this numerical values may be slightly changed.

In order to form the optical member including the quantum dots, the quantum dots emitting RGB colors, which are the three primary colors of the light, or RYGB colors are spin-coated or printed on a transparent substrate, such as a glass substrate. If the quantum dot emitting the yellow color is added, the white light approximate to natural light can be obtained. A matrix (medium) which disperses and carries the quantum dots may emit the light having the visible ray band and the ultraviolet ray band (including far UV band) and may employ an inorganic substance or a polymer representing superior transmittance for the light having the visible ray band. For instance, the organic substance or the polymer may include inorganic silica, polymethylmethacrylate (PMMA), polydimethylsiloxane (PDMS), poly lactic acid (PLA), silicon polymer or YAG.

A display device employing such a quantum dot is disclosed in Korean Unexamined Patent Publication No. 10-2011-0012246.

DISCLOSURE OF INVENTION

Technical Problem

The embodiment provides an optical member having improved reliability and durability, a display device and a method of fabricating the same.

Solution to Problem

An optical member according to the embodiment includes a first substrate; a wavelength conversion layer on the first substrate; and a second substrate on the wavelength conversion layer, wherein the wavelength conversion layer includes an oxygen barrier.

A display device according to the embodiment includes a light source; a wavelength conversion member to which light emitted from the light source is incident; and a display panel to which light output from the wavelength conversion member is incident, wherein the wavelength conversion member includes a first substrate; a wavelength conversion layer on the first substrate; and a second substrate on the wavelength conversion layer, and wherein the wavelength conversion layer includes a phosphor.

A method of fabricating an optical member according to the embodiment includes the steps of forming a wavelength conversion layer including an oxygen barrier on the first substrate; forming a second substrate on the wavelength conversion layer; and heat-treating the wavelength conversion layer.

Advantageous Effects of Invention

The optical member and the display device according to the embodiment include the oxygen barrier contained in the wavelength conversion layer. Thus, the amount of oxygen introduced into the wavelength conversion layer can be reduced and the wavelength conversion particles included in the wavelength conversion layer may not be modified.

In particular, the oxygen barrier is diffused by heat and bonded with a polymer included in the first substrate and/or the second substrate. Thus, air-tightness of the first and second substrates can be improved, so the optical member and the display device according to the embodiment may have the improved reliability.

In addition, the oxygen barrier includes the flame retardant. Thus, the oxygen barrier can be bonded with the polymer contained in the first and second substrates and/or the wavelength conversion layer during the heat treatment process. Therefore, the optical member and the display device according to the embodiment may have the superior oxygen barrier characteristic and heat-resistance characteristic.

As a result, the optical member and the display device according to the embodiment may have superior durability and reliability.

BRIEF DESCRIPTION OF DRAWINGS

FIG. 1 is an exploded perspective view showing a liquid crystal display according to the first embodiment;

FIG. 2 is a perspective view showing a wavelength conversion member according to the first embodiment;

FIG. 3 is a sectional view taken along line A-A' of FIG. 2;

FIG. 4 is an exploded perspective view showing a liquid crystal display according to the second embodiment;

FIG. 5 is a perspective view showing a wavelength conversion member according to the second embodiment;

FIG. 6 is a sectional view taken along line B-B' of FIG. 5;

FIG. 7 is a sectional view showing a light guide plate, a light emitting diode and a wavelength conversion member according to the second embodiment;

FIGS. 8 to 10 are views showing the method of fabricating a wavelength conversion member according to the second embodiment;

FIG. 11 is an exploded perspective view showing a liquid crystal display according to the third embodiment;

FIG. 12 is a perspective view showing a wavelength conversion member according to the third embodiment;

FIG. 13 is a sectional view taken along line C-C' of FIG. 12; and

FIG. 14 is a sectional view showing a light guide plate, a light emitting diode and a wavelength conversion member according to the fourth embodiment.

MODE FOR THE INVENTION

In the description of the embodiments, it will be understood that when a substrate, a frame, a sheet, a layer or a pattern is referred to as being "on" or "under" another substrate, another frame, another sheet, another layer, or another pattern, it can be "directly" or "indirectly" on the other substrate, frame, sheet, layer, or pattern, or one or more intervening layers may also be present. Such a position of the layer has been described with reference to the drawings. The thickness and size of each layer shown in the drawings may be exaggerated, omitted or schematically drawn for the purpose of convenience or clarity. In addition, the size of elements does not utterly reflect an actual size.

FIG. 1 is an exploded perspective view showing a liquid crystal display according to the first embodiment, FIG. 2 is a perspective view showing a wavelength conversion member according to the first embodiment, and FIG. 3 is a sectional view taken along line A-A' of FIG. 2.

Referring to FIGS. 1 to 3, the liquid crystal display (LCD) according to the embodiment includes a backlight unit 10 and a liquid crystal panel 20.

The backlight unit 10 supplies light to the liquid crystal panel 20. The backlight unit 10 serves as a surface light source so that the light can be uniformly supplied to a bottom surface of the liquid crystal panel 20.

The backlight unit 10 is disposed below the liquid crystal panel 20. The backlight unit 10 includes a bottom cover 100, a light guide plate 200, a reflective sheet 300, a light source, such as a plurality of light emitting diodes 400, a printed circuit board 401, and a plurality of optical sheets 500.

The upper portion of the bottom cover 100 is open. The bottom cover 100 receives the light guide plate 200, the light emitting diodes 400, the printed circuit board 401, the reflective sheet 300, and the optical sheets 500 therein.

The light guide plate 200 is disposed in the bottom cover 100 and arranged on the reflective sheet 300. The light guide plate 200 guides the light upward by totally-reflecting, refracting and scattering the light incident thereto from the light emitting diodes 400.

The reflective sheet 300 is disposed below the light guide plate 200. In more detail, the reflective sheet 300 is disposed between the light guide plate 200 and the bottom surface of the bottom cover 100. The reflective sheet 300 reflects the light upward as the light is output downward from the bottom surface of the light guide plate 200.

The light emitting diodes 400 serve as a light source for generating the light. The light emitting diodes 400 are disposed at one lateral side of the light guide plate 200. The light generated from the light emitting diodes 400 is incident into the light guide plate 200 through the lateral side of the light guide plate 200.

The light emitting diodes 400 may include a blue light emitting diode generating the blue light or a UV light emitting diode generating the UV light. In detail, the light emitting diodes 400 may emit the blue light having the wavelength band of about 430 nm to about 470 nm or the UV light having the wavelength band of about 300 nm to abut 400 nm.

The light emitting diodes 400 are mounted on the printed circuit board 401. The light emitting diodes 400 may be disposed under the printed circuit board 401. The light emitting diodes 400 are driven by receiving a driving signal through the printed circuit board 401.

The printed circuit board 401 is electrically connected to the light emitting diodes 400. The printed circuit board 401 may mount the light emitting diodes 400 thereon. The printed circuit board 401 is disposed in the bottom cover 100.

The optical sheets 500 are disposed on the light guide plate 200. The optical sheets 500 supplies the light to the liquid crystal panel 20 by changing or enhancing the optical property of the light output from the top surface of the light guide plate 200.

The optical sheets 500 may include a wavelength conversion member 501, a diffusion sheet 502, a first prism sheet 503, and a second prism sheet 503.

The wavelength conversion member 501 is provided on a light path between the light source 400 and the liquid crystal panel 20. For instance, the wavelength conversion member 501 is provided on the light guide plate 200. In detail, the wavelength conversion member 501 is interposed between the light guide plate 200 and the diffusion sheet 502. The wavelength conversion member 501 converts the wavelength of the incident light and outputs the incident light upward.

For instance, if the light emitting diodes 400 are blue light emitting diodes, the wavelength conversion member 501 converts the blue light output upward from the light guide plate 200 into the green light and the red light. In detail, the wavelength conversion member 501 converts a part of the blue light into the green light having the wavelength in the range of about 520 nm to about 560 nm, and a part of the blue light into the red light having the wavelength in the range of about 630 nm to about 660 nm.

Therefore, the white light may be generated by the light passing through the wavelength conversion member 501 without being converted and the lights converted by the wavelength conversion member 501. In detail, the white light can be incident into the liquid crystal panel 20 through the combination of the blue light, the green light and the red right.

In other words, the wavelength conversion member 501 is an optical member that converts the characteristic of the incident light. The wavelength conversion member 501 may have a sheet shape. That is, the wavelength conversion member 501 is an optical sheet.

As shown in FIGS. 2 and 3, the wavelength conversion member 501 includes a lower substrate 510, an upper substrate 520, a wavelength conversion layer 530, and a sealing part 540.

The lower substrate 510 is provided under the wavelength conversion layer 530. The lower substrate 510 may be transparent and flexible. The lower substrate 510 may adhere to a bottom surface of the wavelength conversion layer 530.

The upper substrate 520 is disposed on the wavelength conversion layer 530. The upper substrate 520 may be transparent and flexible. The upper substrate 520 may adhere to the top surface of the wavelength conversion layer 530.

The wavelength conversion layer 530 is sandwiched between the upper and lower substrates 520 and 510. The upper and lower substrates 520 and 510 support the wavelength conversion layer 530. The upper and lower substrates 520 and 510 protect the wavelength conversion layer 530 from external physical impact. The upper and lower substrates 520 and 510 directly make contact with the wavelength conversion layer 530.

In addition, the upper and lower substrates 520 and 510 have low oxygen permeability and low moisture permeability. Thus, the upper and lower substrates 520 and 510 can protect the wavelength conversion layer 530 from external chemical impact by oxygen and/or moisture.

The wavelength conversion layer 530 is interposed between the lower and upper substrates 510 and 520. The wavelength conversion layer 530 may adhere to the top surface of the lower substrate 510, and adhere to the bottom surface of the upper substrate 520.

The wavelength conversion layer 530 includes a host layer 531 and a plurality of wavelength conversion particles 532. In addition, the wavelength conversion layer 530 may further include an oxygen barrier.

The host layer 531 surrounds the wavelength conversion particles 532. That is, the wavelength conversion particles 532 are uniformly distributed in the host layer 531. The host layer 531 may include a polymer, such as a silicon resin. The host layer 531 is transparent. That is, the host layer 531 may be formed by using a transparent polymer.

The host layer 531 is interposed between the lower and upper substrates 510 and 520. In more detail, the host layer 531 adheres to the top surface of the lower substrate 510 and the bottom surface of the upper substrate 520.

The wavelength conversion particles 532 are interposed between the lower and upper substrates 510 and 520. In more detail, the wavelength conversion particles 532 are uniformly distributed in the host layer 531, and the host layer 531 is interposed between the lower substrate 510 and the upper substrate 520. The wavelength conversion particles 532 may be distributed in the host layer 531 in the concentration of about 0.5 wt % to about 5 wt %.

The wavelength conversion particles 532 convert the wavelength of the light emitted from the light emitting diodes 400. In detail, the wavelength conversion particles 532 receive light emitted from the light emitting diodes 400 to convert the wavelength of the incident light. For instance, the wavelength conversion particles 532 may convert the blue light emitted from the light emitting diodes 400 into the green light and the red light. That is, the wavelength conversion particles 532 may convert the blue light into the green light having the wavelength in the range of about 500 nm to about 600 nm or into the red light having the wavelength in the range of about 630 nm to about 660 nm.

The wavelength conversion particles 532 may include compound semiconductors. In detail, the wavelength conversion particles 532 may include nano particles including the compound semiconductors. In more detail, the wavelength conversion particles 532 may include quantum dots (QD). The quantum dots may include core nano-crystals and shell nano-crystals surrounding the core nano-crystals. In addition, the quantum dots may include organic ligands bonded to the shell nano-crystals. Further, the quantum dots may include an organic coating layer surrounding the shell nano-crystals.

The shell nano-crystals may be prepared as at least two layers. The shell nano-crystals are formed on the surface of the core nano-crystals. The quantum dots lengthen the wavelength of the light incident into the core nano-crystals by using the shell nano-crystals forming a shell layer, thereby improving the light efficiency.

The quantum dots may include at least one of a group-II compound semiconductor, a group-III compound semiconductor, a group-V compound semiconductor, and a group-VI compound semiconductor. In more detail, the core nano-crystals may include CdSe, InGaP, CdTe, CdS, ZnSe, ZnTe, ZnS, HgTe or HgS. In addition, the shell nano-crystals may include CuZnS, CdSe, CdTe, CdS, ZnSe, ZnTe, ZnS, HgTe or HgS. The quantum dot may have a diameter of about 1 nm to about 10 nm.

The wavelength of the light emitted from the quantum dots can be adjusted according to the size of the quantum dots. The organic ligand may include pyridine, mercapto alcohol, thiol, phosphine and phosphine oxide. The organic ligand may stabilize the unstable quantum dots after the synthesis process. Dangling bonds may be formed at the valence band and the quantum dots may be unstable due to the dangling bonds. However, since one end of the organic ligand is the non-bonding state, the one end of the organic ligand is bonded with the dangling bonds, thereby stabilizing the quantum dots.

In particular, if the size of the quantum dot is smaller than the Bohr radius of an exciton, which consists of an electron and a hole excited by light and electricity, the quantum confinement effect may occur, so that the quantum dot may have the discrete energy level. Thus, the size of the energy gap is changed. In addition, the charges are confined within the quantum dot, so that the light emitting efficiency can be improved.

Different from general fluorescent pigments, the fluorescent wavelength of the quantum dot may vary depending on the size of the particles. In detail, the light has the shorter wavelength as the size of the particle is reduced, so that the fluorescent light having the wavelength band of visible ray can be generated by adjusting the size of the particles. In addition, the quantum dot represents the extinction coefficient which is 100 to 1000 times higher than that of the general pigment and has the superior quantum yield as compared with the general pigment, so that strong fluorescent light can be generated.

The quantum dots can be synthesized through the chemical wet scheme. The chemical wet scheme is to grow the particles by immersing the precursor material in the organic solvent. According to the chemical wet scheme, the quantum dots can be synthesized.

The oxygen barrier is included in the wavelength conversion layer 530. In detail, the oxygen barrier is distributed in the wavelength conversion layer 530. In addition, the oxygen barrier can be contained in the first substrate 510 and/or the second substrate 520.

The oxygen barrier is used to improve the oxygen barrier characteristic and the heat-resistance characteristic of the lower substrate 510, the upper substrate 520 and/or the wavelength conversion layer 530. In detail, the oxygen barrier is bonded with the polymer included in the lower substrate 510, the upper substrate 520 and/or the wavelength conversion layer 530 to improve the oxygen barrier characteristic and the heat-resistance characteristic of the lower substrate 510, the upper substrate 520 and/or the wavelength conversion layer 530. In more detail, the oxygen barrier is diffused and decomposed by heat so that the oxygen barrier can be bonded with the polymer included in the lower substrate 510, the upper substrate 520 and/or the wavelength conversion layer 530.

The oxygen barrier may include a flame retardant. For instance, the oxygen barrier can be selected from a halogen-based flame retardant and a phosphor-based flame retardant. In detail, the oxygen barrier may include the phosphor-based flame retardant. In more detail, the oxygen barrier may include a phosphate-based flame retardant.

The oxygen barrier can be expressed as following chemical formula 1.

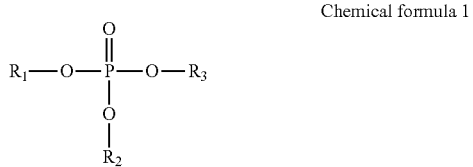

Chemical formula 1

In chemical formula 1, P is phosphor, O is oxygen, and R1, R2 and R3 are independently selected from oxygen, a substituted or non-substituted aryl group, a substituted or non-substituted alkoxy group, and a substituted or non-substituted hetero aryl group. In detail, the R1, R2 and R3 are a substituted or non-substituted aryl group.

The oxygen barrier may include bisphenol-A bis(diphenyl phosphate) expressed as following chemical formula 2.

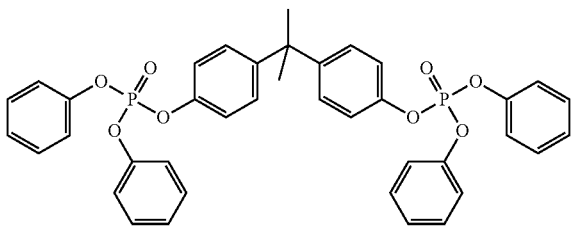

Chemical formula 2

In addition, the oxygen barrier may include resorcinol bis(diphenyl phosphate) expressed as following chemical formula 3.

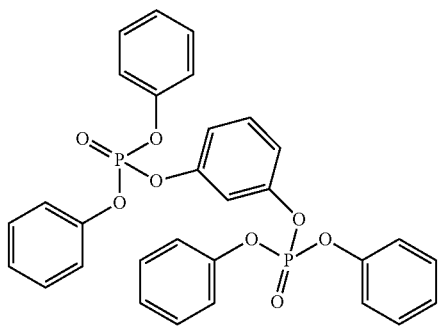

Chemical formula 3

Further, the oxygen barrier may include the phosphor-based flame retardant, such as Ammonium Polyphosphate (APP), Tris(2-chloroethyl)Phosphate (TCEP), Isopropylphenyl Diphenyl Phosphate (IPPP), Triphenyl Phosphate (TPP), Triethyl Phosphate (TEP), Resorcinol di phosphate (RDP), or Tricresyl Phosphate (TCP).

The oxygen barrier can be decomposed into the radical in the high-temperature condition. Especially, if the oxygen barrier is the phosphor-based flame retardant, the oxygen barrier may be decomposed at the temperature of about 100° C. to about 250° C.

The lower substrate 510 and the upper substrate 520 may include a transparent polymer, such as polyethylene terephthalate. In addition, the lower substrate 510 and/or the upper substrate 520 may include a polymer bonded with radicals decomposed from the oxygen barrier.

For instance, the lower substrate 510 and/or the upper substrate 520 may include a polymer substituted with radicals derived from the oxygen barrier. In detail, the lower substrate 510 and/or the upper substrate 520 may include a polymer including a functional group containing phosphor. In more detail, the lower substrate 510 and/or the upper substrate 520 may include a polymer substituted with a phosphite group. For instance, the lower substrate 510 and/or the upper substrate 520 may include substituted polyethylene terephthalate expressed as following chemical formula 4.

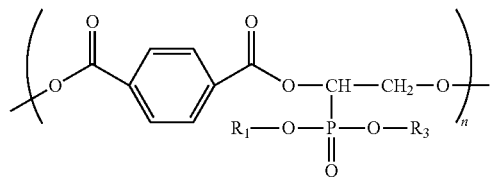

Chemical formula 4

In chemical formula 4, R1 and R3 are independently selected from oxygen, a substituted or non-substituted aryl group, a substituted or non-substituted alkoxy group, and a substituted or non-substituted hetero aryl group. In detail, the R1 and R3 are a substituted or non-substituted aryl group. In addition, n is in the range of 1 to 10,000.

In contrast, the lower substrate 510 and/or the upper substrate 520 may include a polymer substituted with a phosphate group.

The sealing part 540 is disposed at the lateral side of the wavelength conversion layer 530. In detail, the sealing part 540 covers the lateral side of the wavelength conversion layer 530. In more detail, the sealing part 540 can also be disposed at the lateral sides of the lower substrate 510 and the upper substrate 520. In this case, the sealing part 540 covers the lateral sides of the lower substrate 510 and the upper substrate 520.

In addition, the sealing part 540 may be bonded to the lateral sides of the wavelength conversion layer 530, the lower substrate 510 and the upper substrate 520. In addition, the sealing part 540 may closely adhere to the lateral sides of the wavelength conversion layer 530, the lower substrate 510 and the upper substrate 520.

Therefore, the sealing part 540 can seal the lateral side of the wavelength conversion layer 530. That is, the sealing part 540 may serve as a protective part for protecting the wavelength conversion layer 530 from the external chemical impact.

The wavelength conversion member 501 can be formed through the following process.

First, wavelength conversion particles 532 and the oxygen barrier are uniformly distributed in the silicon resin, epoxy resin or acryl resin. At this time, the oxygen barrier can be mixed in the ratio of about 0.1 wt % to about 5 wt %.

Then, the resin composition is uniformly coated on the lower substrate 510. The resin composition may be coated on the top surface of the lower substrate 510 through the slit coating, spin coating or spray coating.

After that, the coated resin composition is cured by light and/or heat, so that the wavelength conversion layer 530 is formed.

Thereafter, the upper substrate 520 is laminated on the upper substrate 520 and then the sealing part 540 is formed.

Then, the wavelength conversion layer 530 is subject to the heat treatment process. Especially, if the oxygen barrier is the phosphor-based flame retardant, the wavelength conversion layer 530 is subject to the heat treatment process for about 10 seconds to about 10 minutes at the temperature of about 100° C. to about 250° C. The temperature and the time of the heat treatment process for the wavelength conversion layer 530 may vary depending on the type of the oxygen barriers.

Therefore, the oxygen barrier included in the wavelength conversion layer 530 is decomposed and diffused by heat. In particular, the oxygen barrier is diffused into the lower substrate 510 and the upper substrate 520. In addition, a part of the oxygen barrier may remain in the wavelength conversion layer 530 without being diffused.

The radical can be formed as the oxygen barrier is decomposed by the heat. The radical is bonded with the polymer included in the lower substrate 510 and/or the upper substrate 520, thereby improving the compactness of the lower substrate 510 and the upper substrate 520. Therefore, the lower substrate 510 and the upper substrate 520 can effectively block the moisture and oxygen introduced thereto from the outside. In addition, since the oxygen barrier includes the flame retardant, the lower substrate 510 and the upper substrate 520 can more effectively block the oxygen introduced thereto from the outside.

Then, the sealing part 540 is formed at the lateral sides of the lower substrate 510, the upper substrate 520 and the wavelength conversion layer 530.

In this manner, the wavelength conversion member 501 can be formed.

In addition, the wavelength conversion member 501 may further include first and second inorganic protective layers. The first inorganic protective layer is coated on the bottom surface of the lower substrate 510 and the second inorganic protective layer is coated on the top surface of the upper substrate 520. The first and second inorganic protective layers may include silicon oxides.

The diffusion sheet 502 is disposed on the wavelength conversion member 501. The diffusion sheet 502 may improve the uniformity of light passing through the diffusion sheet 502. The diffusion sheet 502 may include a plurality of beads.

The first prism sheet 503 is provided on the diffusion sheet 502. The second prism sheet 504 is provided on the first prism sheet 503. The first prism sheet 503 and the second prism sheet 504 may improve the linearity of light passing therethrough.

The liquid crystal panel 20 is disposed on the optical sheets 500. In addition, the liquid crystal panel 20 is disposed on the panel guide 23. The liquid crystal panel 20 is guided by the panel guide 23.

The liquid crystal panel 20 displays images by adjusting intensity of light passing through the liquid crystal panel 20. In detail, the liquid crystal panel 20 is a display panel for displaying the images by using the light emitted from the backlight unit 10. The liquid crystal panel 20 includes a TFT substrate 21, a color filter substrate 22 and a liquid crystal layer interposed between the two substrates. In addition, the liquid crystal panel 20 includes polarizing filters.

Hereinafter, the TFT substrate 21 and the color filter substrate 22 will be described in detail although they are not shown in the drawings in detail. The TFT substrate 21 includes a plurality of gate lines and a plurality of data lines crossing the gate lines to define pixels and a thin film transistor (TFT) is provided at each cross section such that the thin film transistor TFT can be connected to a pixel electrode of the pixel in one-to-one correspondence. The color filter substrate 22 includes color filters having R, G and B colors corresponding to the pixels, a black matrix covering the gate lines, data lines and thin film transistors within the limit of the color filters, and a common electrode covering the above elements.

A driving PCB 25 is provided at an outer peripheral portion of the liquid crystal panel 20 to supply driving signals to the gate lines and data lines.

The driving PCB 25 is electrically connected to the liquid crystal panel 20 by a COF (chip on film) 24. The COF 24 may be replaced with a TCP (tape carrier package).

As described above, in the liquid crystal display, the oxygen barrier is included in the wavelength conversion layer 530. Thus, the amount of oxygen introduced into the wavelength conversion layer 530 can be reduced and the wavelength conversion particles may not be modified.

Especially, the oxygen barrier is diffused by the heat and bonded with the polymer included in the lower substrate 510 and/or the upper substrate 520. Thus, the air-tightness of the lower substrate 510 and the upper substrate 520 can be improved, so the liquid crystal display according to the embodiment may have the improved reliability.

In addition, since the flame retardant is used as the oxygen barrier, the oxygen barrier may be bonded with the polymer included in the lower substrate 510, the upper substrate 520 and/or the wavelength conversion layer 530 during the heat treatment process. Therefore, the wavelength conversion member 501 may have the superior oxygen barrier characteristic and the heat-resistance characteristic.

As a result, the liquid crystal display according to the embodiment may have the improved durability and reliability.

FIG. 4 is an exploded perspective view showing a liquid crystal display according to the second embodiment, FIG. 5 is a perspective view showing a wavelength conversion member according to the second embodiment, FIG. 6 is a sectional view taken along line B-B' of FIG. 5, FIG. 7 is a sectional view showing a light guide plate, a light emitting diode and a wavelength conversion member according to the second embodiment, and FIGS. 8 to 10 are views showing the method of fabricating a wavelength conversion member according to the second embodiment. In the description about the second embodiment, the description about the liquid crystal display according to the previous embodiment will be basically incorporated by reference except for the modified parts.

Referring to FIGS. 4 to 7, the wavelength conversion member 600 is disposed between the light emitting diodes 400 and the light guide plate 200.

The wavelength conversion member 600 may extend in one direction. In detail, the wavelength conversion member 600 may extend along one lateral side of the light guide plate 200. In more detail, the wavelength conversion member 600 may extend along an incident surface of the light guide plate 200.

The wavelength conversion member 600 receives light emitted from the light emitting diodes 400 to convert the wavelength of the incident light. For instance, the wavelength conversion member 600 may convert the blue light emitted from the light emitting diodes 400 into the green light and the red light. That is, the wavelength conversion member 600 may convert a part of the blue light into the green light having the wavelength in the range of about 520 nm to about 560 nm and convert a part of the blue light into the red light having the wavelength in the range of about 630 nm to about 660 nm.

Therefore, the white light may be generated by the light passing through the wavelength conversion member 600 and the lights converted by the wavelength conversion member 600. In detail, the white light can be incident into the light guide plate 200 through the combination of the blue light, the green light and the red right.

As shown in FIGS. 5 to 7, the wavelength conversion member 600 includes a lower substrate 610, an upper substrate 620, a wavelength conversion layer 630, and a sealing part 640.

As shown in FIG. 6, the lower substrate 610 is provided under the wavelength conversion layer 630. The lower substrate 610 may be transparent and flexible. The lower substrate 610 may adhere to a bottom surface of the wavelength conversion layer 630.

The upper substrate 620 is disposed on the wavelength conversion layer 630. The upper substrate 620 may be transparent and flexible. The upper substrate 620 may adhere to the top surface of the wavelength conversion layer 630.

In addition, as shown in FIG. 7, the lower substrate 610 faces the light emitting diodes 400. That is, the lower substrate 610 is disposed between the light emitting diodes 400 and the wavelength conversion layer 630. In addition, the upper substrate 620 faces the light guide plate 200. That is, the upper substrate 620 is disposed between the wavelength conversion layer 630 and the light guide plate 200.

The wavelength conversion layer 630 is sandwiched between the upper and lower substrates 620 and 610. In addition, the sealing part 640 covers the lateral side of the wavelength conversion layer 630. The upper and lower substrates 620 and 610 support the wavelength conversion layer 630. In addition, the upper and lower substrates 620 and 610 and the sealing part 540 may protect the wavelength conversion layer 630 from the external physical and chemical impact.

The wavelength conversion member according to the present embodiment can be formed through the following process.

Referring to FIG. 8, a resin composition including a plurality of wavelength conversion particles 632 and the oxygen barrier is coated on a first transparent substrate 611. Then, the resin composition is cured by light and/or heat so that a preliminary wavelength conversion layer 635 is formed on the first transparent substrate 611.

Then, a second transparent substrate 621 is laminated on the preliminary wavelength conversion layer 635.

After that, the preliminary wavelength conversion layer 635 is subject to the heat treatment process and the oxygen barrier included in the preliminary wavelength conversion layer 635 is diffused and decomposed by the heat. In addition, the decomposed oxygen barrier is bonded with the polymer included in the first transparent substrate 611 and/or the second transparent substrate 621.

Referring to FIG. 9, the first transparent substrate 611, the preliminary wavelength conversion layer 635 and the second transparent substrate 621 are simultaneously cut. Therefore, a plurality of preliminary wavelength conversion members 601 can be formed. Each of the preliminary wavelength conversion members 601 may include the lower substrate 610, the wavelength conversion layer 630 and the upper substrate 620. Since the lower substrate 610, the wavelength conversion layer 630 and the upper substrate 620 are simultaneously cut through the cutting process, the lower substrate 610, the wavelength conversion layer 630 and the upper substrate 620 may have cutting surfaces 605 aligned on the same plane.

Referring to FIG. 10, the preliminary wavelength conversion members 601 are aligned such that the lower substrate 610 may face the upper substrate 620. Then, the sealing part 640 is formed at the lateral sides of the preliminary wavelength conversion members 601, that is, at the cutting surface 605.

After that, the wavelength conversion members 601 may be separated from each other.

In the liquid crystal display according to the present embodiment, the wavelength conversion layer 630 has a relatively small size. Thus, a smaller amount of wavelength conversion particles 632 can be used to fabricate the liquid crystal display according to the present embodiment.

Therefore, the liquid crystal display according to the present embodiment can reduce the amount of the wavelength conversion particles 632 and can be readily fabricated at the low cost.

FIG. 11 is an exploded perspective view showing a liquid crystal display according to the third embodiment. FIG. 12 is a perspective view showing a wavelength conversion member according to the third embodiment. FIG. 13 is a sectional view taken along line C-C' of FIG. 12. FIG. 14 is a sectional view showing a light guide plate, a light emitting diode and a wavelength conversion member according to the third embodiment. In the description about the third embodiment, the description about the liquid crystal display according to the previous embodiments will be basically incorporated by reference except for the modified parts.

Referring to FIGS. 11 to 14, the liquid crystal display according to the present embodiment includes a plurality of wavelength conversion members 700. The wavelength conversion members 700 correspond to the light emitting diodes 400, respectively.

In addition, the wavelength conversion members 700 are disposed between the light emitting diodes 400 and the light guide plate 200. That is, each of the wavelength conversion members 700 is disposed between the corresponding light emitting diode and the light guide plate 200.

The wavelength conversion members 700 may have surface areas larger than surface areas of the light emitting diodes 400. Thus, most of the light emitted from each light emitting diode may be incident into the corresponding wavelength conversion member 700.

In addition, as shown in FIGS. 12 to 14, each of the wavelength conversion members 700 may include a lower substrate 710, an upper substrate 720, a wavelength conversion layer 730 and a sealing part 740.

The features of the lower substrate 710, the upper substrate 720, the wavelength conversion layer 730 and the sealing part 740 are substantially identical to those of the previous embodiments.

In the liquid crystal display according to the present embodiment, the wavelength conversion layer 730 has a relatively small size. Thus, a smaller amount of wavelength conversion particles 732 can be used to fabricate the liquid crystal display according to the present embodiment.

Therefore, the liquid crystal display according to the present embodiment can reduce the amount of the wavelength conversion particles 732 and can be readily fabricated at the low cost.

In addition, the feature of each wavelength conversion member 700 can be modified suitably for the corresponding light emitting diode 400. Thus, the liquid crystal display according to the embodiment may have the superior reliability, brightness, and color reproduction.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effects such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The invention claimed is:

1. An optical member comprising:
    a wavelength conversion layer; a first substrate under the wavelength conversion layer;
    a second substrate on the wavelength conversion layer;
    a first inorganic protective layer coated on a bottom surface of the first substrate;
    a second inorganic protective layer coated on a top surface of the second substrate; and
    a sealing part disposed at a lateral surface of the wavelength conversion layer,
    wherein the wavelength conversion layer includes an oxygen barrier,
    wherein the wavelength conversion layer comprises a host and quantum dots in the host,
    wherein the host includes a silicon resin,
    wherein the first and second inorganic protective layers include a silicon oxide,
    wherein the first and second substrates include a polyethylene terephthalate,
    wherein the first and second substrates are transparent,
    wherein the first substrate comprises a top surface, the bottom surface, and a lateral surface connecting the top surface to the bottom surface;
    wherein the second substrate comprises the top surface, a bottom surface, and a lateral surface connecting the top surface to the bottom surface;
    wherein the top surface of the first substrate is in direct physical contact with a bottom surface of the host,
    wherein the bottom surface of the second substrate is in direct physical contact with a top surface of the host,
    wherein the sealing part is in direct physical contact with a lateral surface of the host,
    wherein the sealing part is in direct physical contact with the lateral surface of the first substrate and the lateral surface of the second substrate,
    wherein the quantum dots are distributed in the host in a concentration of 0.5 wt % to 5 wt % based on a total content of the wavelength conversion layer,
    wherein the oxygen barrier is distributed in the host in a concentration of 0.1 wt % to 5 wt % based on a total content of the wavelength conversion layer,
    wherein the wavelength conversion layer is subjected to a heat treatment process at a temperature of 100° C. to 250° C., wherein the oxygen barrier included in the wavelength conversion layer is decomposed by heat, and wherein the oxygen barrier is diffused into the first and second substrates by heat, and a part of the oxygen barrier remains in the host;
    wherein radicals are formed as the oxygen barrier is decomposed by the heat, and the radicals bond with a polymer included in the first substrate, a polymer included in the second substrate, and a polymer included in host; and
    wherein each of the first substrate and the second substrate includes substituted polyethylene terephthalate expressed as the following chemical formula 4:

Chemical formula 4

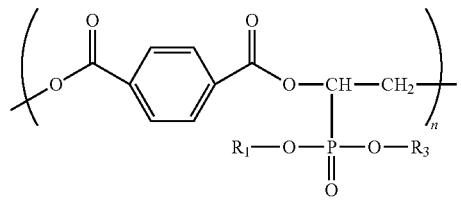

where each of $R_1$ and $R_3$ is a substituted or non-substituted aryl group, and n is in a range of from 1 to 10,000.

2. The optical member of claim 1, wherein the oxygen barrier includes a flame retardant containing a phosphor.

3. The optical member of claim 1, wherein the first substrate or the second substrate includes a phosphor.

4. The optical member of claim 3, wherein the first substrate or the second substrate includes a polymer having a phosphite group.

* * * * *